(12) United States Patent
Takasaki

(10) Patent No.: US 9,820,712 B2
(45) Date of Patent: Nov. 21, 2017

(54) RADIATION IMAGING APPARATUS AND CONTROL METHOD AND PROGRAM OF THE APPARATUS

(71) Applicant: CANON KABUSHIKI KAISHA, Tokyo (JP)

(72) Inventor: Takashi Takasaki, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/264,273

(22) Filed: Sep. 13, 2016

(65) Prior Publication Data

US 2017/0000439 A1    Jan. 5, 2017

Related U.S. Application Data

(63) Continuation of application No. 13/522,399, filed as application No. PCT/JP2011/000383 on Jan. 25, 2011, now Pat. No. 9,492,134.

(30) Foreign Application Priority Data

Jan. 27, 2010 (JP) ................................. 2010-015855

(51) Int. Cl.
*A61B 6/00*    (2006.01)

(52) U.S. Cl.
CPC .............. *A61B 6/5205* (2013.01); *A61B 6/40* (2013.01); *A61B 6/405* (2013.01); *A61B 6/42* (2013.01); *A61B 6/465* (2013.01); *A61B 6/469* (2013.01); *A61B 6/481* (2013.01); *A61B 6/482* (2013.01); *A61B 6/486* (2013.01); *A61B 6/5217* (2013.01); *A61B 6/54* (2013.01); *A61B 6/542* (2013.01); *A61B 6/545* (2013.01); *A61B 6/461* (2013.01); *A61B 6/5211* (2013.01)

(58) Field of Classification Search
CPC .................................. A61B 6/482; G06T 5/50
USPC .............................. 378/5, 98.9, 98.11, 98.12
See application file for complete search history.

(56) References Cited

U.S. PATENT DOCUMENTS

| | | | | |
|---|---|---|---|---|
| 3,894,181 A * | 7/1975 | Mistretta | .................. | G21K 4/00 348/E5.089 |
| 4,029,963 A * | 6/1977 | Alvarez | ................. | A61B 6/032 250/360.1 |
| 4,813,061 A * | 3/1989 | Kakegawa | ............... | H05G 1/60 250/583 |
| 6,925,144 B2 * | 8/2005 | Matsumoto | ............ | A61B 6/032 378/22 |
| 7,274,771 B2 * | 9/2007 | Allred | .................... | A61B 6/032 378/108 |

(Continued)

*Primary Examiner* — Michael Maskell
(74) *Attorney, Agent, or Firm* — Canon USA Inc., IP Division

(57) ABSTRACT

An energy control unit continuously adjusts energy of radiations in one shot emitted by an X-ray irradiation unit. An X-ray detection unit generates a plurality of image data pieces in one shot by detecting the radiations whose energy is continuously adjusted and transmitted through a subject. An image classification unit classifies the plurality of image data pieces generated by the X-ray detection unit into image data generated by the radiations of a high energy side and image data generated by the radiations of a low energy side. An image subtraction unit performs weighting and subtraction on the image data generated by the radiations of the high energy side and the image data generated by the radiations of the low energy side.

27 Claims, 8 Drawing Sheets

(56) References Cited

U.S. PATENT DOCUMENTS

| | | | |
|---|---|---|---|
| 2002/0085671 A1* | 7/2002 | Sakaida | A61B 6/4241 378/98.11 |
| 2003/0169850 A1* | 9/2003 | Kump | A61B 6/405 378/207 |
| 2009/0060312 A1* | 3/2009 | Kitamura | G06T 5/50 382/132 |
| 2010/0232566 A1* | 9/2010 | Hirokawa | A61B 6/032 378/5 |
| 2014/0211909 A1* | 7/2014 | Yamazaki | A61B 6/032 378/4 |
| 2016/0143603 A1* | 5/2016 | Hoffman | A61B 6/482 378/5 |

* cited by examiner

RADIATION IMAGING APPARATUS AND CONTROL METHOD AND PROGRAM OF THE APPARATUS

CROSS-REFERENCE TO RELATED APPLICATIONS

This application is a Continuation of U.S. patent application Ser. No. 12/522,399, filed Jul. 16, 2012, which is a U.S. national stage application of International Patent Application No. PCT/JP2011/000383, filed Jan. 25, 2011, which claims the priority benefit of Japanese Patent Application No. 2010-015855 filed Jan. 27, 2010, all of which are hereby incorporated by reference herein in their entirety.

TECHNICAL FIELD

The present invention relates to a technique for shooting an image of a subject using radiation.

BACKGROUND ART

An energy subtraction method is an image shooting method for improving visualization of an interest region using a difference of X-ray absorption characteristics of a material depending on energy of the X-rays. More specifically, in the method, a subject is irradiated with X-ray beams having high energy and X-ray beams having low energy, the respective X-ray beams transmitted through the subject are captured as X-ray image data by an image detection unit, and energy subtraction image data is generated by subtracting both of the X-ray image data pieces.

Further, the interest region can be changed by changing a weight to the X-ray image data captured by the high-energy X-ray beams and a weight to the X-ray image data captured by the low-energy X-ray beams. By the change, energy subtraction image data in which tissue of bone portions is erased and soft tissue is extracted as an interest region, and in an opposite manner, energy subtraction image data in which the soft tissue is erased and the bone portion is extracted as the interest region can be obtained.

In the generation of the energy subtraction image data, if each of the energy of the high-energy X-ray beam and the low-energy X-ray beam is not appropriate, the interest region cannot be appropriately extracted. Thus, various methods have been discussed to solve the problem.

In Japanese Patent Application Laid-Open No. 2007-222311, at least in image shooting using the high energy X-ray beam, the energy is discretely changed at a plurality of steps, and X-ray image data is captured at each step. Then, subtraction processing is performed using at least two or more combinations of the X-ray image data captured by the high-energy X-ray beam and the X-ray image data captured by the low-energy X-ray beam, respectively. By this processing, as compared to a case in which only one shot of the X-ray image data captured by the high-energy X-ray beam and one shot of the X-ray image data captured by the low-energy X-ray beam are captured, the possibility of obtaining energy subtraction image data captured with appropriate energy is increased.

However, when the X-ray image data is captured by discretely changing the energy, if there is appropriate energy other than the discrete energy, it is not possible to obtain appropriate energy subtraction image data. Accordingly, in the case of the technique discussed in Japanese Patent Application Laid-Open No. 2007-222311, energy subtraction image data captured with appropriate energy may not be obtained in a single shooting.

CITATION LIST

Patent Literature

[PTL 1]
Japanese Patent Application Laid-Open No. 2007-222311

SUMMARY OF INVENTION

Solution to Problem

The present invention is directed to obtaining a plurality of pieces of energy subtraction image data in a single shooting.

According to an aspect of the present invention, a radiation imaging apparatus includes an irradiation unit configured to irradiate a subject with radiations, a control unit configured to continuously adjust energy of the radiations in one shot emitted by the irradiation unit, a generation unit configured to generate a plurality of image data pieces in one shot by detecting the radiations whose energy is continuously adjusted by the control unit and transmitted through the subject, a classification unit configured to classify the plurality of image data pieces generated by the generation unit into image data generated by the radiations of a high energy side and image data generated by the radiations of a low energy side, and a subtraction unit configured to perform weighting and subtraction on the image data generated by the radiations of the high energy side and the image data generated by the radiations of the low energy side.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

In the following descriptions of exemplary embodiments of the present invention, it is described a case an X-ray imaging apparatus that performs imaging of X-ray image data of a subject using the X-ray that is a kind of radiation is applied as a radiation imaging apparatus according to the exemplary embodiments of the present invention. The exemplary embodiment of the present invention is not limited to the X-ray imaging apparatus. For example, the exemplary embodiment of the present invention can be applied to a radiation imaging apparatus that performs imaging of a radiation image of a subject using the other radiation such as alpha rays, beta rays, or gamma rays.

Figure 1:
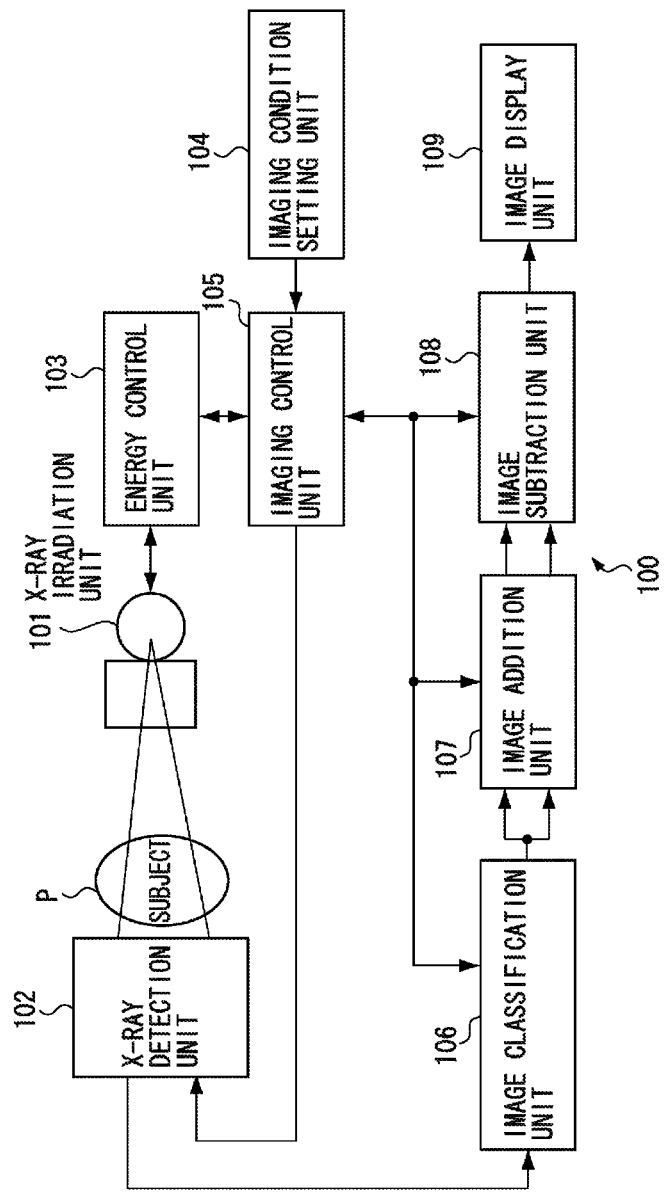
FIG. 1 illustrates a configuration of an X-ray imaging apparatus according to an exemplary embodiment of the present invention.

A first exemplary embodiment of the present invention is described. FIG. 1 illustrates an overall configuration of an X-ray imaging apparatus 100 according to the first exemplary embodiment of the present invention. The X-ray imaging apparatus 100 is specially used for medical purposes.

In FIG. 1, an X-ray irradiation unit 101 irradiates a subject P with X-rays. An X-ray detection unit 102 detects X-rays that transmitted through the subject P, and generates X-ray image data. The X-ray irradiation unit 101 includes an X-ray generation unit (tube) (not shown) that generates X-rays, and a collimator that defines a beam spreading angle of the X-rays generated in the X-ray generation unit. The X-ray detection unit 102 is formed by arranging fine solid-state image sensors two-dimensionally in grid-like manner.

An energy control unit 103 controls energy of the X-rays emitted from the X-ray irradiation unit 101. The energy control unit 103 can continuously adjust the energy of the X-rays in one shot that is emitted from the X-ray irradiation unit 101. An imaging condition setting unit 104 sets imaging conditions such as energy, a frame rate, and binning of the X-rays with which the subject is irradiated in response to an operation by an operator.

An image classification unit 106 classifies a plurality of sheets of the X-ray image data captured by the X-ray detection unit 102 into an X-ray image data group that is captured with high-energy X-ray beams and an X-ray image data group that is captured with low-energy X-ray beams.

An image addition unit 107 performs weighting on each X-ray image data included in the same group to each of the X-ray image data group that is captured with the high-energy X-ray beams and the X-ray image data group that is captured with the low-energy X-ray beams classified by the image classification unit 106. The image addition unit 107 performs addition to the weighted X-ray image data in the same group.

An image subtraction unit 108 performs weighting on the X-ray image data that is captured with the high-energy X-ray beams and the X-ray image data that is captured with the low-energy X-ray beams that are added by the image addition unit 107 respectively, and performs subtraction on the data. An image display unit 109 outputs the X-ray image data subtracted by the image subtraction unit 108 to a monitor or the like.

The X-ray irradiation unit 101 is an example of an irradiation unit according to the present invention. The energy control unit 103 is an example of a control unit according to the present invention. The X-ray detection unit 102 is an example of a generation unit according to the present invention. The image classification unit 106 is an example of a classification unit according to the present invention. The image subtraction unit 108 is an example of a subtraction unit according to the present invention. The image addition unit 107 is an example of an addition unit according to the present invention.

Figure 2A:
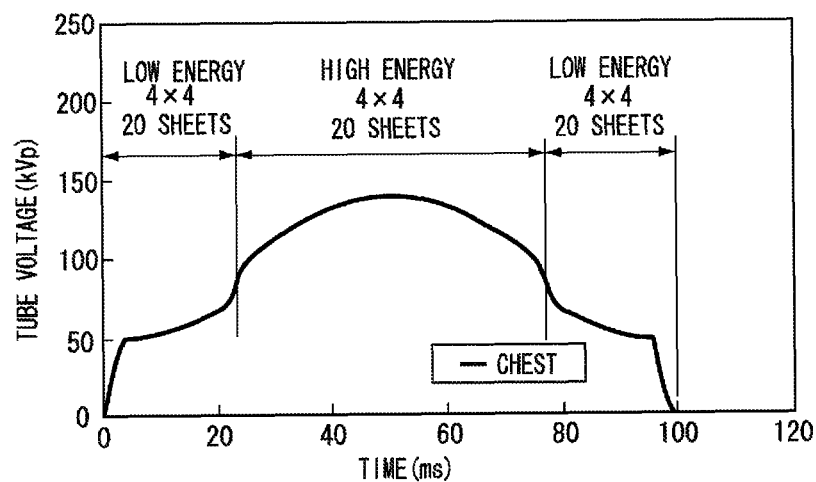
FIG. 2A illustrates time change in X-ray energy in one shot of the X-rays from an X-ray irradiation unit with which a subject is irradiated and the number of shots of X-ray image data to be captured by one shot of the X-rays.

Next, with reference to FIG. 2A, time change in the X-ray energy in one shot of the X-rays from the X-ray irradiation unit 101 with which the subject P is irradiated and the number of shots of the X-ray image data to be captured by one shot of the X-rays. FIG. 2A illustrates a case in which imaging for separating soft tissue and bone portions is performed in chest radiography. In FIG. 2A, a tube voltage of an X-ray tube in one shot of the X-ray is continuously controlled. Further, in FIG. 2A, phases of a shot of the X-ray image data by the X-ray detection unit 102 and change in the tube voltage are shifted by an imaging control unit 105 between a case in which the tube voltage increases as time advances and a case in which the tube voltage decreases as time advances.

Furthermore, in FIG. 2A, high frame rate imaging is performed by performing 4*4 binning. Accordingly, in FIG. 2A, X-ray image data of the subject irradiated with different X-ray energy including 20 sheets of the X-ray image data captured with the high-energy X-ray beams and 20 sheets of the X-ray image data captured with the low-energy X-ray beams can be obtained in irradiation time of 100 ms of one shot of the X-rays. The binning is a method for reading a predetermined number of pixels (in the above exemplary example, 4*4) for detecting radiation as one unit.

Figure 3A:
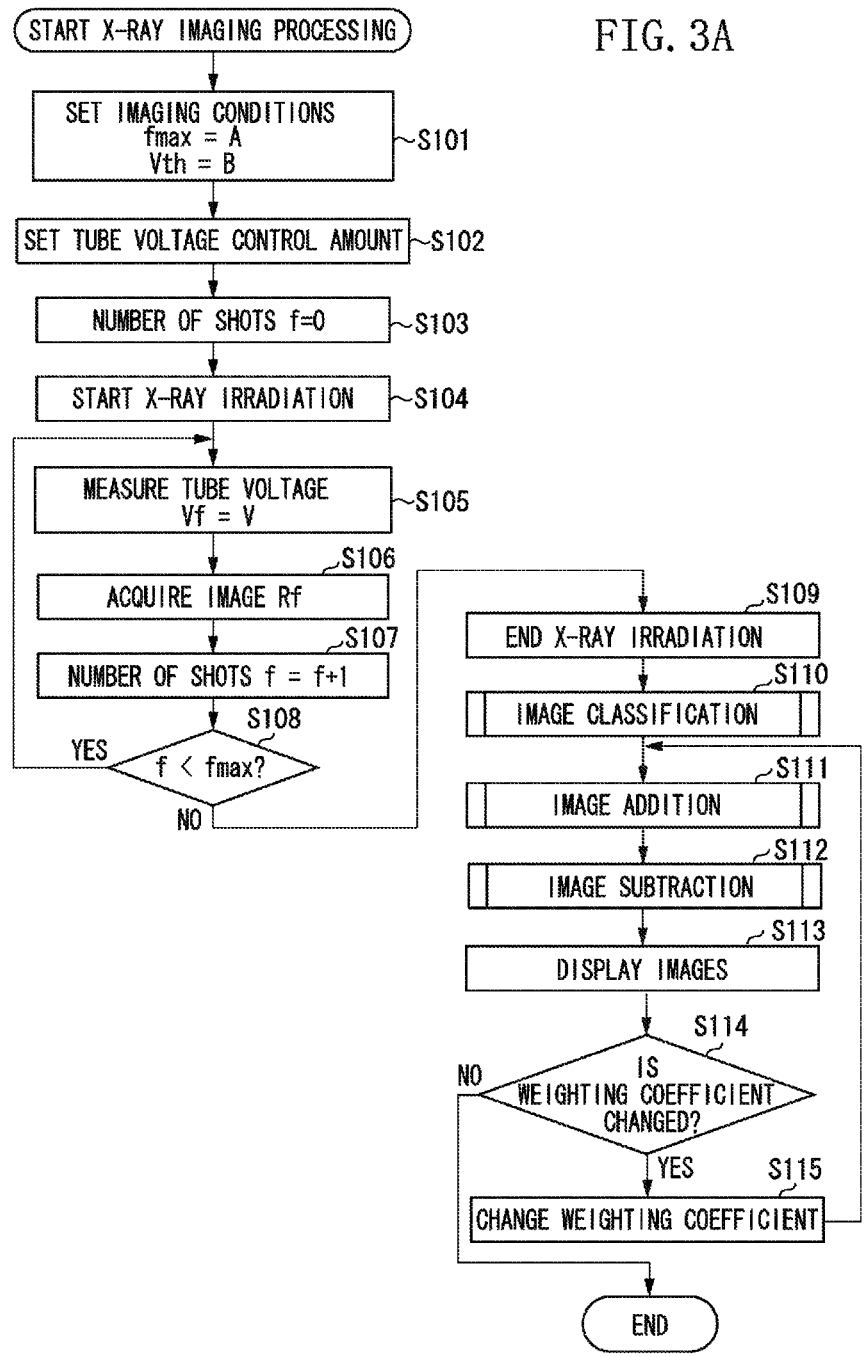
FIG. 3A is a flowchart illustrating processing in the X-ray imaging apparatus according to the exemplary embodiment of the present invention.

With reference to a flowchart in FIG. 3A, the flow of the X-ray imaging processing in the X-ray imaging apparatus 100 is described. In FIG. 3A, a variable fmax is the number of shots of the X-ray image data (the number of X-ray image shots) set by an operator. A variable Vth is a threshold value of the tube voltage for distinguishing between the X-ray image data captured with the high-energy X-ray beams and the X-ray image data captured with the low-energy X-ray beams. A variable f is the number of shots of X-ray image data from the start of imaging. A variable Vf is a tube voltage applied to the tube in shooting of X-ray image data at the variable f.

In FIG. 3A, in step S101, the imaging condition setting unit 104 sets imaging conditions for shooting an image of a subject in response to an operation of the operator. The imaging conditions may include the number of shots of the X-ray image fmax, high and low tube voltages that are determined to be appropriate, the threshold value Vth of the tube voltage for distinguishing between the X-ray image data captured with the high-energy X-ray beams and the X-ray image data captured with the low-energy X-ray beams, and the like.

Then, in step S102, the imaging control unit 105 determines a tube voltage waveform for one shot of the X-ray as shown in FIG. 2A such that many shots of the X-ray image data at small tube voltage differences can be obtained around the tube voltage that is inputted by the operator and considered to be appropriate. Then, the imaging control unit 105 transmits a tube voltage control signal of the tube voltage waveform to the energy control unit 103.

In step S103, the imaging control unit 105 sets the variable f to an initial value zero. In step S104, the energy control unit 103 starts irradiation of the X-ray to the subject according to the tube voltage control signal in step S102.

In step S105, the imaging control unit 105 records the tube voltage waveform as Vf at the variable f determined in step S102. In step S106, the X-ray detection unit 102 detects the X-rays transmitted through the subject, and the detection result is stored as X-ray image data Rf. In step S107, the imaging control unit 105 adds one to the variable f to update the number of the X-ray image data pieces captured up until then.

In step S108, the imaging control unit 105 determines whether the value of the variable f is smaller than the value of the variable fmax to determine whether the number of the captured X-ray image data pieces captured up until then reaches the number of X-ray image shots set by the operator.

If the number of the X-ray image data pieces captured up until then reaches the number of X-ray image shots set by the operator (NO in step S108), the processing proceeds to step S109. Or if the number of the X-ray image data pieces captured up until then has not reached yet the number of X-ray image shots (YES in step S108), the processing returns to step S105. In step S109, the energy control unit 103 stops the X-ray irradiation to the subject by the X-ray irradiation unit 101.

The shooting of the first shot of the X-ray image data in step S106 is performed at the same time or before the X-ray irradiation in step S104 is performed. The shooting of the last shot of the X-ray image data in step S106 is performed until the X-ray irradiation in step S109 is completed.

In step S110, the image classification unit 106 classifies the X-ray image data pieces captured in step S106 into a group of the X-ray image data captured with the high-energy X-ray beams and a group of the X-ray image data captured with the low-energy X-ray beams.

In step S111, the image addition unit 107 performs addition of the X-ray image data by weighting to each X-ray image data in the group with respect to the X-ray image data pieces classified into the same group in step S110.

In step S112, the image subtraction unit 108 performs subtraction of the X-ray image data by weighting to both of the X-ray image data captured with the high-energy X-ray beams and the X-ray image data captured with the low-energy X-ray beams added in step S111. Processing performed in steps S110, S111, and S112 is described below in detail.

In step S113, the image display unit 109 displays the X-ray image data subtracted in step S112 on a monitor, or the like. The operator can check the X-ray image data displayed in step S113, and determine whether appropriate X-ray image data is obtained. If the operator determines that the appropriate X-ray image data is obtained, the operator performs an end operation. If the operator determines that the appropriate X-ray image data is not obtained, the operator performs an operation to change the weighting coefficient.

In step S114, the imaging control unit 105 determines whether the operation to change the weighting coefficient is performed. If the operation to change the weighting coefficient is performed (YES in step S114), the processing returns to step S111. Or if not the operation to change the weighting coefficient, but the end operation is performed (NO in step S114), the processing ends. The above-described steps 111 to 115 will be repeated until the operator determines the appropriate X-ray image data is obtained. By the above-described operation, the appropriate energy subtraction image data can be obtained.

Next, the flows of the image classification, the image addition, and the image subtraction are described with reference to the flowchart in FIG. 3B.

Figure 3B:
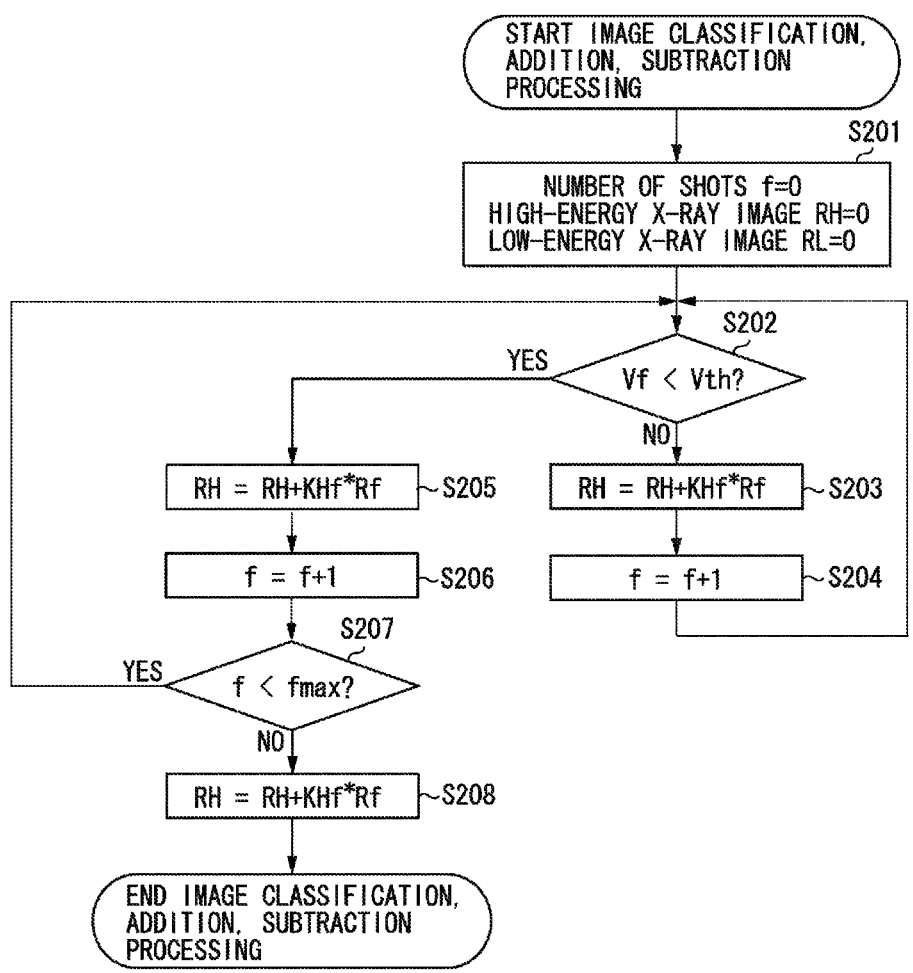
FIG. 3B is a flowchart illustrating processing in the X-ray imaging apparatus according to the exemplary embodiment of the present invention.

In FIG. 3B, a variable RH is the X-ray image data captured with the high-energy X-ray beams. A variable RL is the X-ray image data captured with the low-energy X-ray beams. A variable R is the X-ray image data obtained by performing the weighting and the subtraction to the X-ray image data pieces. Variables kHf and kLf are weighting coefficients for the respective X-ray image data pieces used in the addition of the X-ray image data captured with the high-energy X-ray beams and the X-ray image data captured with the low-energy X-ray beams. Variables kH and kL are weighting coefficients for the respective X-ray image data pieces used in the subtraction of the X-ray image data RH and the X-ray image data RL.

In step S201, the imaging control unit 105 returns the variable f to zero. Further, the imaging control unit 105 substitutes the initial value zero for all pixel values of the X-ray image data RH captured with the high-energy X-ray beams and the X-ray image data RL captured with the low-energy X-ray beams.

In step S202, the imaging control unit 105 determines whether the value of the variable Vf is smaller than the value of the variable Vth. In other words, the imaging control unit 105 determines whether the tube voltage Vf at the time of shooting the X-ray image data Rf is lower than the threshold value Vth. If the tube voltage Vf at the time of shooting the X-ray image data Rf is lower than the threshold value Vth (YES in step S202), the processing proceeds to step S205. On the other hand, if the tube voltage Vf at the time of shooting the X-ray image data Rf is equal to or greater than the threshold value Vth (NO in step S202), the processing proceeds to step S203.

In step S203, the imaging control unit 105 multiplies the X-ray image data Rf by the weighting coefficient kHf, and adds the weighted value to the X-ray image data RH. Thus, the X-ray image data captured with the high-energy X-ray beams is added. In step S204, the imaging control unit 105 adds one to the variable f to update the captured image that is the target of the addition.

In step S205, the imaging control unit 105 multiplies the X-ray image data Rf by the weighting coefficient kLf, and adds the weighted value to the X-ray image data RL. Thus, the X-ray image data captured with the low-energy X-ray beams is added. In step S206, the imaging control unit 105 adds one to the variable f to update the captured image that is the target of the addition. In step S207, the imaging control unit 105 determines whether the value of the variable f is smaller than the value of the number of X-ray image shots fmax. If the value of the variable f is smaller than the value of the number of X-ray image shots fmax (YES in step S207), the processing returns to step S202. Then, the processing from step S202 to step S206 is repeated until the last shot.

If the value of the variable f is equal to the value of the number of X-ray image shots fmax (NO in step S207), the processing proceeds to step S208. In step S208, the imaging control unit 105 multiplies the X-ray image data RH and the X-ray image data RL by the variables kH and kL respectively, and subtracts the both values. By the operation, difference image data between the X-ray image data captured with the high-energy X-ray beams and the X-ray image data captured with the low-energy X-ray beams can be obtained.

In the processing of the image classification, the image addition, and the image subtraction, initial values of the weighting coefficients kHf, kLf, kH, and kL of the X-ray image data can be any value. Further, as the initial values of the weighting coefficients kHf, kLf, kH, and kL, a plurality of combinations of these values can be made. Using each of the combinations, the processing from step S201 to step S208 can be performed, and a plurality of pieces of difference image data of different weighting coefficients can be generated. Then, these data pieces can be displayed on the display, and the operator can select an optimum image.

By the above-described processing, 20 sheets each of the X-ray image data of different irradiation X-ray energy groups, namely the high-energy side and the low-energy side, can be obtained at one shot of X-ray irradiation. Moreover, the operator can freely select the weighting coefficients in the addition of the X-ray image data at the high-energy side and the X-ray image data at the low-energy side respectively and the weighting coefficients in the subtraction of the X-ray image data at the high-energy side and the X-ray image data at the low-energy side. By this operation, the appropriate energy subtraction image data can be surely obtained in a single shooting.

A second exemplary embodiment of the present invention is described. An X-ray imaging apparatus according to the present exemplary embodiment has a configuration similar to that in the first exemplary embodiment shown in FIG. 1. However, functions of the imaging control unit 105 are different therefrom as described below.

In the first exemplary embodiment, the description is based on the assumption that the imaging region is the chest and the imaging is performed without using a contrast agent. Further, an age of a subject is not considered, and the binning in the single shooting is fixed. Moreover, the operator adjusts the parameters for performing the weighting of the X-ray image data to obtain appropriate energy subtraction image data.

In the second exemplary embodiment, it is possible to perform switching of the imaging region, imaging using a contrast agent, imaging by considering the age of the subject, and imaging by changing the binning in the single shooting. Further, an automatic adjustment function of the weighting coefficient for obtaining appropriate X-ray image data is provided.

For these purposes, the imaging control unit 105 according to the second exemplary embodiment includes a function for partially reading the X-ray image data, a region recognition function for recognizing a region based on the X-ray image data, and an interest region recognition function for recognizing an interest region of the X-ray image data and peripheral regions of the interest region based on a result of the region recognition by the region recognition function and imaging conditions set by the operator.

Figure 4:
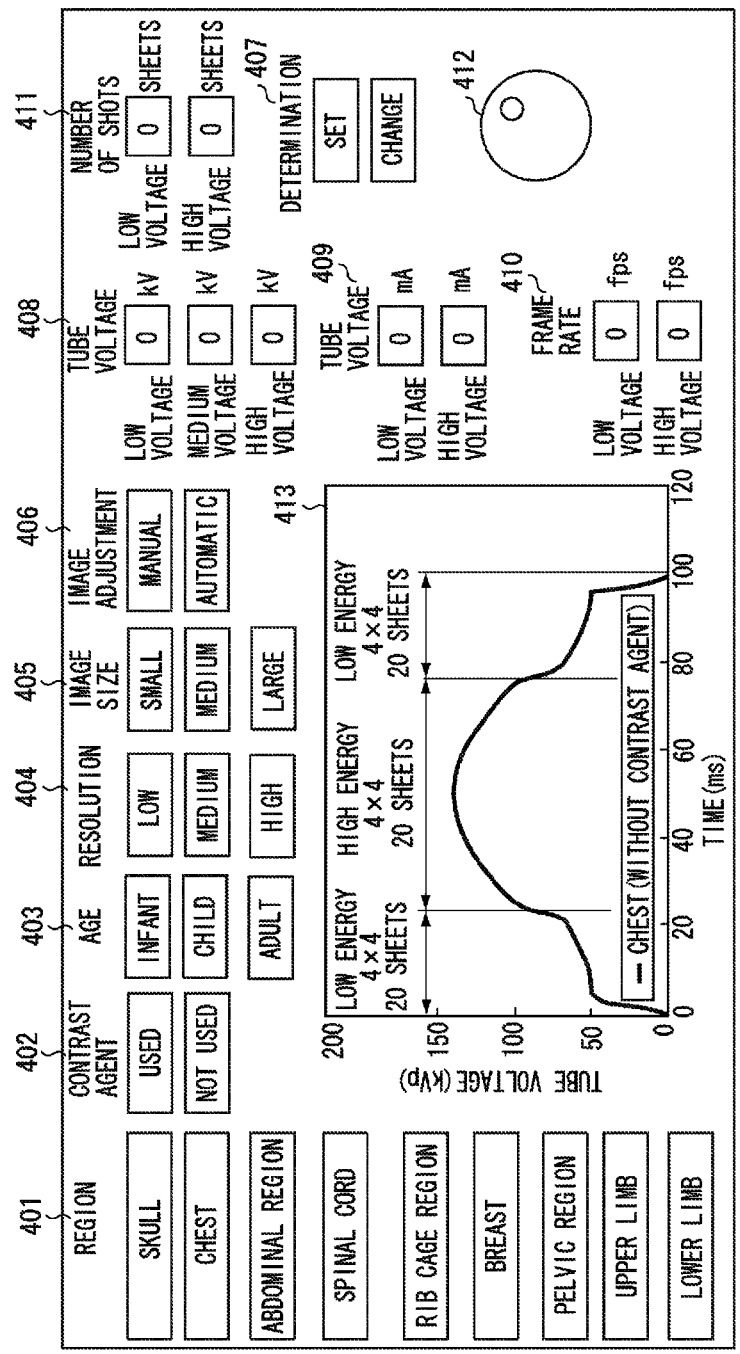
FIG. 4 illustrates a button layout on an operation screen displayed by a function of an imaging condition setting unit.

With reference to FIG. 4, the imaging condition setting unit 104 according to the second exemplary embodiment is described. FIG. 4 illustrates an example of a button layout on an operation screen displayed by the functions of the imaging condition setting unit 104 according to the second exemplary embodiment. The operation screen displayed by the imaging condition setting unit 104 includes selection buttons 401 to 407 for selecting a region, a contrast agent, an age, a resolution, an image size, image adjustment, and determination. Moreover, the operation screen includes adjustment windows 408 to 411 for tube voltage, tube current, a frame rate, and the number of shots, an adjustment dial 412, and a tube voltage waveform display window 413.

In the second exemplary embodiment, an operator inputs imaging conditions in the order of the region, the contrast agent, the age, the resolution, and the image size on the operation screen shown in FIG. 4. Then, at each step, a time change waveform of the tube voltage, binning, and the number of shots are displayed on the tube voltage waveform display window. Via each selection button and the adjustment window, the imaging conditions can be manually adjusted at each step. When the SET button is pressed, the conditions are inputted into the imaging control unit 105, and imaging can be performed under the conditions. Even after the SET button is pressed, the imaging conditions can be set again by pressing the CHANGE button.

Figure 2B:
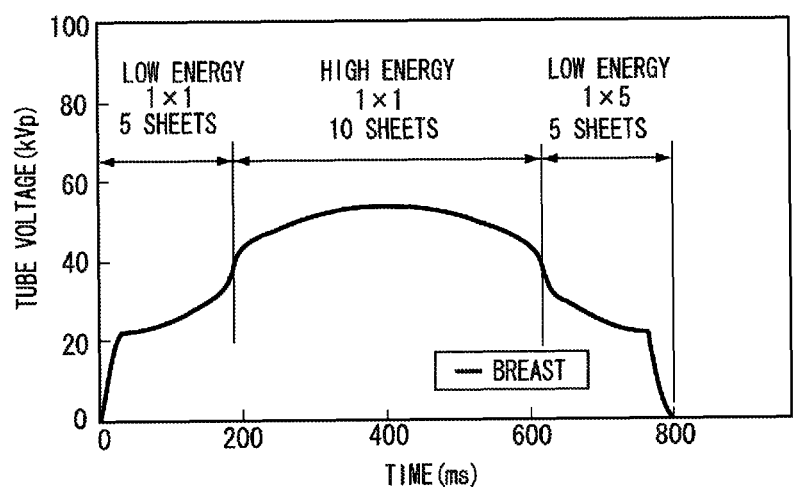
FIG. 2B illustrates time change in X-ray energy in one shot of the X-rays from an X-ray irradiation unit with which a subject is irradiated and the number of shots of X-ray image data to be captured by one shot of the X-rays.

Next, with reference to FIGS. 2B to 2E, imaging conditions automatically set as initial values when each selection button on the operation screen shown in FIG. 4 are described. FIG. 2B shows imaging conditions set to the imaging control unit 105 as initial values when a breast is selected as the region in FIG. 4.

The tube voltage in FIG. 2B is set to a value lower than that of the case for the imaging of the chest is FIG. 2A in order to erase mammary glands and to improve visualization of a tumor mass. Further, high-resolution imaging without binning is performed. As described above, in the second exemplary embodiment, the tube voltage and the binning can be changed depending on the imaging region.

Figure 2C:
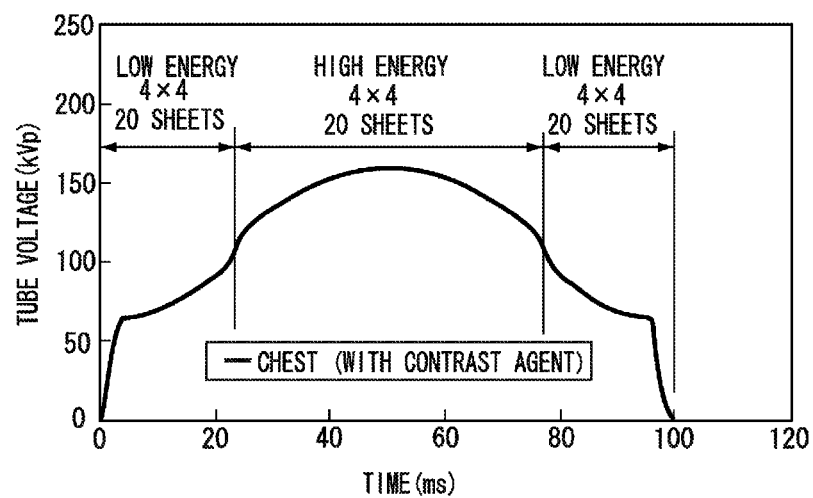
FIG. 2C illustrates time change in X-ray energy in one shot of the X-rays from an X-ray irradiation unit with which a subject is irradiated and the number of shots of X-ray image data to be captured by one shot of the X-rays.

FIG. 2C shows imaging conditions set to the imaging control unit 105 as initial values when a chest is selected as the region and use of a contrast agent is selected on the operation screen shown in FIG. 4. In FIG. 2C, in order to separate the contrast agent and bone portions, the tube voltage is set to a higher value as compared to the case of not using the contrast agent in FIG. 2A. As described above, in the second exemplary embodiment, the tube voltage can be changed depending on the use or nonuse of the contrast agent.

Figure 2D:
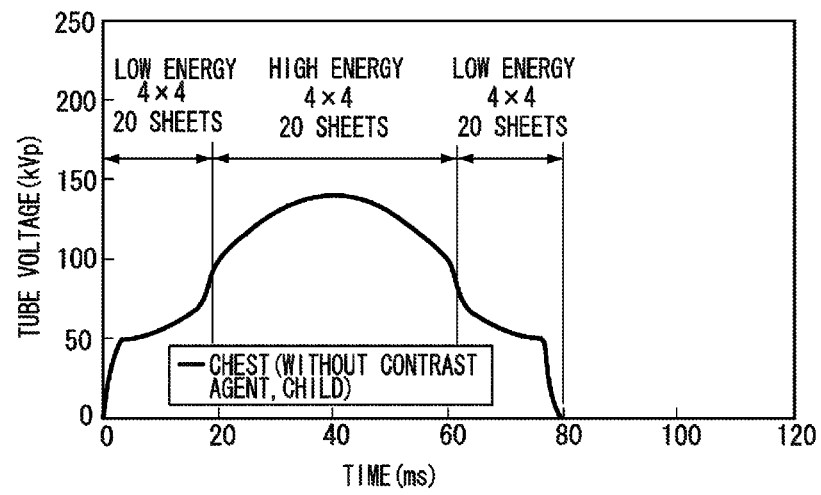
FIG. 2D illustrates time change in X-ray energy in one shot of the X-rays from an X-ray irradiation unit with which a subject is irradiated and the number of shots of X-ray image data to be captured by one shot of the X-rays.

FIG. 2D shows imaging conditions set to the imaging control unit 105 as initial values when a chest is selected as the region, nonuse of the contrast agent is selected, and child is selected as the age on the operation screen shown in FIG. 4. In FIG. 2D, since child's heartbeat is normally faster than that of adults and imaging in shorter time is required, the tube voltage is controlled such that the imaging time is shorter than that in the case of the adult shown in FIG. 2A. Moreover, in FIG. 2D, the imaging control unit 105 performs partial reading of the image to increase the frame rate that can be captured, and performs the imaging such that the energy resolution is not decreased as compared to the case in FIG. 2A. In the imaging of the child, the resolution can be decreased by binning as compared to the imaging of the adult, and the frame rate can be increased instead.

As described above, in the second exemplary embodiment, the partial reading of the X-ray image data, or the imaging with increased frame rate by binning can be performed depending on the age of the subject. The above-described processing of increasing the frame rate of the image data that is partially read as compared to the rate before the partial reading is performed, and the processing of increasing the frame rate after the resolution is decreased as compared to the rate before the resolution is decreased by binning are examples of processing of s changing unit according to the present invention.

Figure 2E:
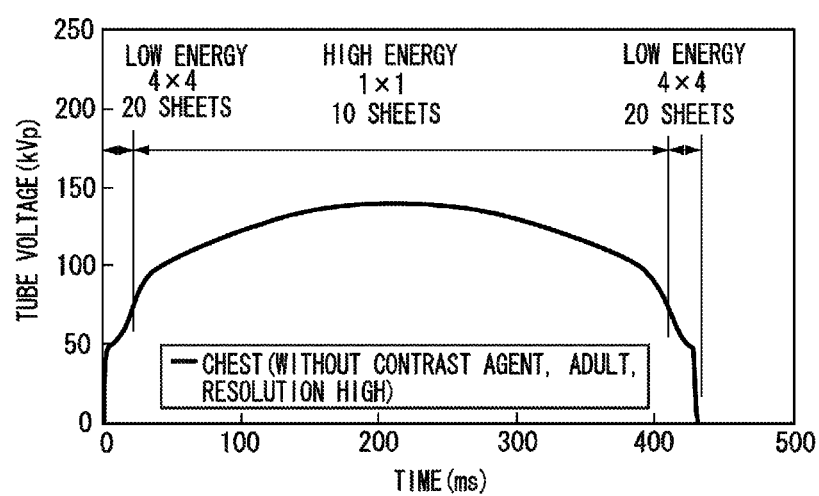
FIG. 2E illustrate time change in X-ray energy in one shot of the X-rays from an X-ray irradiation unit with which a subject is irradiated and the number of shots of X-ray image data to be captured by one shot of the X-rays.

FIG. 2E shows imaging conditions set to the imaging control unit 105 as initial values when a chest is selected as the region, nonuse of the contrast agent is selected, adult is selected as the age, and high is selected as the resolution on the operation screen shown in FIG. 4.

In FIG. 2E, the X-ray image data captured with the low-energy X-ray beams is generally hard to see the fine structure and deterioration in the image quality due to binning is small. Accordingly, imaging of the X-ray image data captured with the high-energy X-ray beams is performed by binning of 1*1, and imaging of the X-ray image data captured with the low-energy X-ray beams is performed by binning of 4*4. By changing the resolution by binning in the irradiation of the X-ray one shot, the imaging time can be shortened as compared to the imaging of binning of 1*1 with the high energy or the low energy, and a motion artifact can be reduced. As described above, in the second exemplary embodiment, binning can be changed in the single shooting.

A difference in shooting processing between the first exemplary embodiment and the second exemplary embodiment is described. The difference in the shooting processing between the first exemplary embodiment and the second exemplary embodiment is in the imaging condition setting processing in step S101 in the case that the image adjustment is manually set on the operation screen shown in FIG. 4. In the case that the image adjustment is automatically set, the imaging condition setting processing in step S101, the processing of determining the change in the weighting of the X-ray image data in step S114, and the weighting processing in step S115 are different.

Figure 3C:
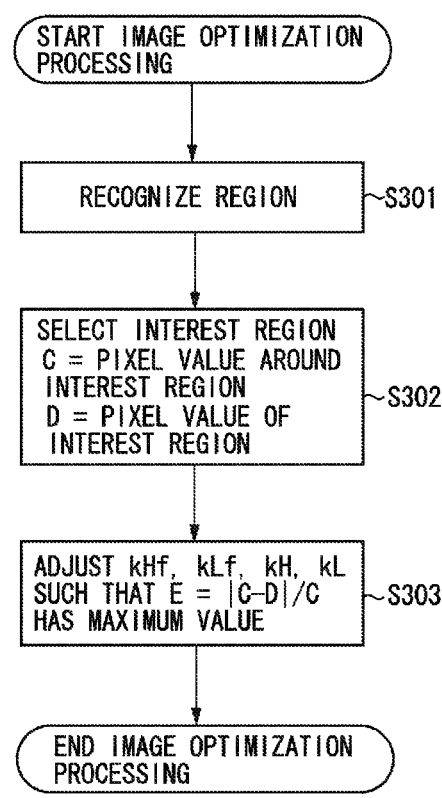
FIG. 3C is a flowchart illustrating processing in the X-ray imaging apparatus according to the exemplary embodiment of the present invention.

Hereinafter, image optimization processing which is alternative processing in steps S114 and 115 when the image adjustment is automatically performed is described with reference to FIG. 3C. The processing of setting the image conditions in step S101 is performed as described above.

In step S301, the imaging control unit 105 performs region recognition by the region recognition function based on the first X-ray image data in step S112, and determines to which region the region of the X-ray image data corresponds. The method of the region recognition can be any method available to the public.

In step S302, the imaging control unit 105 sets an interest region and a peripheral region of the interest region by the interest region recognition function based on the result of the region recognition in step S301 and the imaging conditions set in step S101. The interest region and the peripheral region are, for example, in imaging with the contrast agent, the region of the contrast agent is the interest region and the region around the contrast agent is the peripheral region. The regions are set for each image condition in advance. The interest region and the peripheral region can be selected by the operator from the captured X-ray image data displayed on the monitor or the like. In step S302, the imaging control unit 105 defines a pixel value in the peripheral region as C, and a pixel value in the interest region as D.

In step S303, the imaging control unit 105 calculates the pixel value D in the interest region and the pixel value C in the peripheral region defined in step S302, and adjusts the variables kHf, kLf, kH, and kL such that contrast between these regions becomes maximum. The contrast is defined by the equation $E=|C-D|/C$.

The adjustment method of the variables kHf, kLf, kH, and kL can be any optimization method available to the public. For example, a genetic algorithm can be applied in which maximization of the variable E is set as an objective function and the variables kHf, kLf, kH, and kL are used as design variables. By the processing, the image optimization processing ends, and the operator can check the optimized X-ray image data.

By the above-described processing, as compared to the first exemplary embodiment, more appropriate energy subtraction image data can be obtained with fewer man-hours for the operator.

The exemplary embodiments of the present invention can be implemented by executing the following processing. That is, software (a program) to implement the functions of the above-described exemplary embodiments is supplied to a system or an apparatus via a network or various storage medium. A computer (or central processing unit (CPU) or micro processing unit (MPU)) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-015855 filed Jan. 27, 2010, which is hereby incorporated by reference herein in its entirety.

The invention claimed is:

1. An apparatus for radiation imaging comprising:
an irradiation unit configured to irradiate an object with radiation that tube voltage of the irradiation unit is continuously changed in one shot;
a radiation detector configured to detect radiation, which is irradiated by the irradiation unit, in one shot through the object;
an obtaining unit configured to obtain image data corresponding to a low energy side of a tube voltage waveform in one shot that is a one pulse wave pattern and image data corresponding to a high energy side of the tube voltage waveform in one shot that is the one pulse wave pattern, based on an elapsed time corresponding to radiation that tube voltage of the irradiation unit is continuously changed throughout the one shot; and
a subtraction unit configured to perform subtraction on the image data corresponding to the low energy side and the image data corresponding to the high energy side.

2. The radiation imaging apparatus according to claim 1, wherein the subtraction unit is configured to perform the subtraction on the image data corresponding to the low energy side and the image data corresponding to the high energy side, based on the radiation of the high energy side and the radiation of the low energy side obtained by the radiation detector in one shot.

3. The radiation imaging apparatus according to claim 1, further comprising:
a control unit configured to continuously adjust energy of the radiation in one shot irradiated by the irradiation unit.

4. The radiation imaging apparatus according to claim 1, further comprising:
a classification unit configured to classify the image data corresponding to the low energy side into a first group and the image data corresponding to the high energy side into a second group, based the radiation irradiated by the irradiation unit during the elapsed time; and
an addition unit configured to perform weighting and addition on each image data group classified into the same type by the classification unit, wherein the subtraction unit performs weighting and subtraction on the image data obtained by the radiation of the high energy side and the image data obtained by the radiation of the low energy side.

5. The radiation imaging apparatus according to claim 3, wherein the control unit controls the irradiation unit to irradiate the subject in one shot with radiation having an energy within the low energy side or the high energy side according to an imaging region of the subject.

6. The radiation imaging apparatus according to claim 3, wherein the control unit controls the irradiation unit to irradiate the subject with radiation having an energy within the low energy side or the high energy side according to whether a contrast agent is used or not used for imaging the subject.

7. The radiation imaging apparatus according to claim 1, further comprising:
a changing unit configured to change a frame rate of the image data obtained by the obtaining unit,
wherein the changing unit changes the frame rate based on at least one of an imaging region of the subject and an age of the subject.

8. The radiation imaging apparatus according to claim 7, further comprising:
a partial reading unit configured to perform partial reading of the image data obtained by the obtaining unit,
wherein the changing unit sets the frame rate of the partially read image data higher than the frame rate of the image data before the partial reading is performed.

9. The radiation imaging apparatus according to claim 1, further comprising:
a binning unit included in the obtaining unit and configured to unite a predetermined number of pixels of the radiation detector for detecting radiation in one shot through the object.

10. The radiation imaging apparatus according to claim 1, further comprising:
a binning unit included in the obtaining unit and configured to unite a predetermined number of pixels of the radiation detector for detecting radiation in one shot through the object,
wherein the binning unit changes the number of pixels for uniting while one shot of the radiation is irradiated from the irradiation unit.

11. The radiation imaging apparatus according to claim 10, wherein the binning unit changes the number of pixels for uniting depending on a case in which the image data is obtained with the radiation of the high energy side and a case in which the image data is obtained with the radiation of the low energy side.

12. The radiation imaging apparatus according to claim 1, further comprising:
a changing unit configured to change a frame rate of the image data obtained by the obtaining unit,
wherein the changing unit changes the frame rate of the image data obtained by the obtaining unit while one shot of the radiation is irradiated from the irradiation unit.

13. The radiation imaging apparatus according to claim 10, wherein the changing unit changes the frame rate of the image data obtained by the obtaining unit depending on a case in which the image data is obtained with the radiation of the high energy side and a case in which the image data is obtained with the radiation of the low energy side.

14. The radiation imaging apparatus according to claim 2, wherein the subtraction unit performs weighting such that a contrast of an interest region in the subtraction-processed image data is to be maximum.

15. The radiation imaging apparatus according to claim 1, wherein the control unit determines the tube voltage waveform for one shot based on an imaging condition that is inputted by an operator.

16. The radiation imaging apparatus according to claim 15, wherein the control unit determines the tube voltage waveform for one shot based on the tube voltage that is inputted by the operator.

17. A method for radiation imaging comprising:
irradiating an object with radiation that tube voltage of an irradiation unit is continuously changed in one shot;
detecting, with a radiation detector, radiation which is irradiated by the irradiation unit, in one shot through the object;
obtaining image data corresponding to a low energy side of a tube voltage waveform in one shot that is a one pulse wave pattern and image data corresponding to a high energy side of the tube voltage waveform in one shot that is the one pulse wave pattern, based on an elapsed time corresponding to radiation that tube voltage of the irradiation unit is continuously changed throughout the one shot; and
performing subtraction on the image data corresponding to the low energy side and the image data corresponding to the high energy side.

18. A non-transitory computer-readable storage medium storing thereon a program, which when executed by a computer causes the computer to perform a method for radiation imaging comprising:
irradiating an object with radiation that tube voltage of an irradiation unit is continuously changed in one shot;
detecting, with a radiation detector, radiation which is irradiated by the irradiation unit, in one shot through the object;
obtaining image data corresponding to a low energy side of a tube voltage waveform in one shot that is a one pulse wave pattern and image data corresponding to a high energy side of the tube voltage waveform in one shot that is the one pulse wave pattern, based on an elapsed time corresponding to radiation that tube voltage of the irradiation unit is continuously changed throughout the one shot; and
performing subtraction on the image data corresponding to the low energy side and the image data corresponding to the high energy side.

19. An apparatus for radiation imaging comprising:
a setting unit configured to set a tube voltage waveform that changes continuously throughout one shot;
an irradiation unit configured to irradiate an object with radiation that changes continuously throughout one shot based on the tube voltage waveform set by the setting unit;
a radiation detector configured to detect radiation, which is irradiated by the irradiation unit, in one shot through the object;
an obtaining unit configured to obtain image data corresponding to a low energy side in one shot and image data corresponding to a high energy side in one shot; and
a subtraction unit configured to perform subtraction processing on the image data corresponding to the low energy side and the image data corresponding to the high energy side,
wherein the setting unit sets a threshold value of a tube voltage for distinguishing between the image data corresponding to the low energy side and the image data corresponding to the high energy side, and wherein the obtaining unit obtains the image data corresponding to the low energy side and the image data corresponding to the high energy side based on the threshold value.

20. A method for radiation imaging comprising:
setting a tube voltage waveform that changes continuously throughout one shot;
irradiating an object with radiation of an irradiation unit whose radiation is changed continuously throughout one shot based on the tube voltage waveform set by the setting;
detecting radiation, which is irradiated by the irradiation unit, in one shot through the object;
obtaining image data corresponding to a low energy side in one shot and image data corresponding to a high energy side in one shot;
setting a threshold value of a tube voltage for distinguishing between the image data corresponding to the low energy side and the image data corresponding to the high energy side; and
performing subtraction processing on the image data corresponding to the low energy side and the image data corresponding to the high energy side,
wherein the obtaining image data includes obtaining the image data corresponding to the low energy side and the image data corresponding to the high energy side based on the threshold value.

21. A non-transitory computer-readable medium storing thereon a program, which when executed by a computer causes the computer to perform a method for radiation imaging comprising:
setting a tube voltage waveform that changes continuously throughout one shot;
irradiating an object with radiation, of an irradiation unit whose radiation is changed continuously throughout one shot based on the tube voltage waveform set by the setting;
detecting radiation, which is irradiated by the irradiation unit, in one shot through the object;
obtaining image data corresponding to a low energy side in one shot and image data corresponding to a high energy side in one shot;
setting a threshold value of a tube voltage for distinguishing between the image data corresponding to the low energy side and the image data corresponding to the high energy side; and
performing subtraction processing on the image data corresponding to the low energy side and the image data corresponding to the high energy side,
wherein the obtaining image data includes obtaining the image data corresponding to the low energy side and the image data corresponding to the high energy side based on the threshold value.

22. The radiation imaging apparatus according to claim 1, wherein the tube voltage waveform is a one pulse upward convex wave pattern.

23. The radiation imaging apparatus according to claim 1, wherein the tube voltage waveform is a one pulse wave pattern formed within 100 ms or less.

24. The radiation imaging apparatus according to claim 1, wherein the tube voltage waveform is a one pulse wave pattern in which a change in tube voltage is shifted between a case in which the tube voltage increases as time advances from the start of the one pulse and a case in which the tube voltage decreases as time advances to the end of the one pulse.

25. An apparatus for radiation imaging comprising:
an irradiation unit configured to irradiate an object with radiation that tube voltage of the irradiation unit is changed in one shot within 100 ms or less;
a radiation detector configured to detect radiation, which is irradiated by the irradiation unit, in one shot through the object;
an obtaining unit configured to obtain image data corresponding to a low energy side of a tube voltage waveform in one shot that is a one pulse wave pattern and image data corresponding to a high energy side of the tube voltage waveform in one shot that is the one pulse wave pattern, based on an elapsed time corresponding to radiation that tube voltage of the irradiation unit is changed throughout the one shot within 100 ms or less; and
a subtraction unit configured to perform subtraction on the image data corresponding to the low energy side and the image data corresponding to the high energy side.

26. A method for radiation imaging comprising:
irradiating an object with radiation that tube voltage of an irradiation unit is changed in one shot within 100 ms or less;
detecting radiation, with a radiation detector, which is irradiated by the irradiation unit, in one shot through the object;
obtaining image data corresponding to a low energy side of a tube voltage waveform in one shot that is a one pulse wave pattern and image data corresponding to a high energy side of the tube voltage waveform in one shot that is the one pulse wave pattern, based on an elapsed time corresponding to radiation that tube voltage of the irradiation unit is changed throughout the one shot within 100 ms or less; and
performing subtraction on the image data corresponding to the low energy side and the image data corresponding to the high energy side.

27. A non-transitory computer-readable storage medium storing thereon a program, which when executed by a computer causes the computer to perform a method for radiation imaging comprising:
irradiating an object with radiation that tube voltage of an irradiation unit is changed in one shot within 100 ms or less;
detecting radiation, with a radiation detector, which is irradiated by the irradiation unit, in one shot through the object;
obtaining image data corresponding to a low energy side of a tube voltage waveform in one shot that is a one pulse wave pattern and image data corresponding to a high energy side of the tube voltage waveform in one shot that is the one pulse wave pattern, based on an elapsed time corresponding to radiation that tube voltage of the irradiation unit is changed throughout the one shot within 100 ms or less; and
performing subtraction on the image data corresponding to the low energy side and the image data corresponding to the high energy side.

* * * * *